United States Patent [19] [11] Patent Number: 4,543,362
Berger et al. [45] Date of Patent: Sep. 24, 1985

[54] P-ALKYL OR CYCLOALKYL PHENOXY ALKANOLS AND ALKANOL ESTERS AND PROCESS FOR THE TREATMENT OF ALLERGIC CONDITIONS

[75] Inventors: Frank M. Berger, 190 E. 72nd St., New York, N.Y. 10031; Joseph I. DeGraw, Jr.; Howard L. Johnson, both of Sunnyvale, Calif.

[73] Assignee: Frank M. Berger, New York, N.Y.

[21] Appl. No.: 550,838

[22] Filed: Jan. 13, 1984

Related U.S. Application Data

[60] Division of Ser. No. 327,141, Dec. 3, 1981, Pat. No. 4,451,474, which is a continuation-in-part of Ser. No. 114,183, Jan. 22, 1980, abandoned.

[51] Int. Cl.$^4$ ............................................. A61K 31/27
[52] U.S. Cl. ..................... 514/480; 514/490; 260/463; 546/322; 560/106; 560/163; 568/633; 568/648
[58] Field of Search .................... 560/164; 424/300

[56] References Cited

U.S. PATENT DOCUMENTS 3,759,986 9/1973 Creger ................................. 424/300
4,424,395 1/1984 Strom ................................. 560/164

FOREIGN PATENT DOCUMENTS 2220M 4/1962 France ................................. 560/164
47-3755 2/1972 Japan ................................. 424/300
253656 12/1948 Switzerland ...................... 560/164

OTHER PUBLICATIONS

Akhmedov, Chem. Abst. 78:3899 (1973).
Akhmedov, J. Org. Chem. USSR, 7, p. 117–118 (1971).

Primary Examiner—Michael L. Shippen

[57] ABSTRACT p-Alkyl or cycloalkyl phenoxy alkanols and esters are provided having the structure:

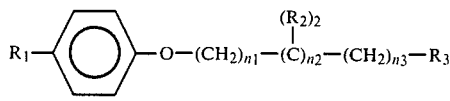

in which:

$R_1$ is an alkyl group having from one to six carbon atoms, preferably tertiary, and still more preferably tertiary-butyl; or a bivalent cycloalkylene group condensed with the phenyl group at adjacent ring carbons thereof, such as in indane;

$R_2$ is lower alkyl having from one to three carbon atoms or hydrogen;

$R_3$ is hydroxyl or an ester group selected from the group consisting of $COOR_4$ and $OOCR_4$ derived from unsubstituted and hydroxy-substituted monocarboxylic acids and $COOR_5OOC$ and $OOCR_5COO$ derived from unsubstituted and hydroxy-substituted dicarboxylic acids, the acids being selected from the group consisting of aliphatic acids, including carbamic acid, having from one to about twelve carbon atoms; cycloaliphatic acids having from three to about twelve carbon atoms; carbocyclic aromatic acids having from six to about twenty carbon atoms; and nitrogen heterocyclic aromatic acids having from five to about twelve carbon atoms, $R_4$ being monovalent aliphatic, cycloaliphatic, aromatic, or nitrogen heterocyclic aromatic, and $R_5$ being divalent aliphatic, cycloaliphatic, aromatic, or nitrogen heterocyclic aromatic, the acids being esterified with aliphatic alcohols having from one to six carbon atoms; and carbonic acid monoalkyl esters, the alkyl having from one to three carbon atoms; and $n_1$, $n_2$ and $n_3$ represent the number of $CH_2$, $C(R_2)_2$ and $CH_2$ groups, respectively, and are numbers within the range from 0 to 10; and at least one of $n_1$, $n_2$ and $n_3$ is other than zero.

These compounds inhibit abnormal tissue reactivity due to specific allergic hypersensitivity or due to specific irritants by inhibiting the release of chemical mediators.

7 Claims, No Drawings

P-ALKYL OR CYCLOALKYL PHENOXY ALKANOLS AND ALKANOL ESTERS AND PROCESS FOR THE TREATMENT OF ALLERGIC CONDITIONS

This is a division of application Ser. No. 327,141, filed Dec. 3, 1981, now U.S. Pat. No. 4,451,474, which in turn is a continuation-in-part of Ser. No. 114,183, filed Jan. 22, 1980, now abandoned.

A person is said to be allergic when he shows hypersensitivity to a substance which is harmless to most other people. This hypersensitivity can manifest itself in many ways, such as, for example, in bronchial asthma, rhinitis, urticaria, eczema, and others. The agent to which the allergic individuals are hypersensitive, i.e., the allergen, stimulates the production of specific antibodies. When an allergen comes into contact with its specific antibody, a number of toxic substances are released from the cell, including, among others, histamine, slow reacting substance A, bradikinin, serotonin, leukokinin, kalikrein, and other kinins and prostaglandins. The release of these toxic substances is responsible for the observed symptoms in all allergic disorders. This field has been reviewed by Kaliner and Austen in *Annual Review of Pharmacology* 15 177–189 (1975).

Various remedies have been prescribed for the treatment of allergies, but no entirely satifactory treatment is available.

The antihistimines decrease the sensitivity of some but not all tissues to histamine, but do not affect the sensitivity of tissues to other toxic substances released during the allergic reaction. The antihistamines do not affect the release of histamine or other toxic substances released during allergic reactions.

Bronchial dilators are used for the symptomatic treatment of asthma, but they have no specific anti-allergenic action.

Corticosteroids decrease inflammatory reactions when given in large doses, but their usefulness in treatment is limited by the serious side effects that accompany their use.

Some compounds are known that affect allergic reactions by inhibiting mediator release, but none of the known substances is broadly effective, and some have toxic side effects.

Cox, *Nature* 216 1328 (Dec. 30, 1967) described the activity of a 4H-1-benzopyran-2-carboxylic acid derivative he called cromolyn sodium or disodium cromoglycate. This compound is ineffective when administered orally, because it is very poorly absorbed from the gastrointestinal tract. For this reason, the compound has to be given by inhalation. In addition, it has a relatively low activity, making the administration of an effective dose impractical. The drug has to be given prophylactically, as it is ineffective when given therapeutically. For these reasons, the compound although known for many years has not been widely used.

Chlorphenesin, a p-chlorophenyl glycerol ether, was reported by Lichtenstein and Atkinson, *The Journal of Immunology* 103 866 (1969), to inhibit histamine release from human leukocytes. Previously, the compound was described by Berger and Bradley, *The British Journal of Pharmacology* 1 265 (1946) as having a muscle-relaxant action, similar to that produced by mephenesin, by a depressant effect on the interneurons of the central nervous system. The antifungal action and antibacterial action of the compound were described by Bergen, Hubbard and Lugwig, *Journal of Applied Microbiology* 1 146 (1953).

Berger, Fukui, Goldenbaum, DeAngelo and Chandlee, *The Journal of Immunology* 102 1024 (1969) reported the effect of the drug on immune responses. Chlorphenesin when given jointly with the antigen suppressed antibody formation. The drug also had an effect on delayed hypersensitivity reactions, when given at the time of challenge.

Chlorphenesin also suppressed passive cutaneous anaphylaxis induced by penicillin, according to Berger, Fukui, Ludwig and Margolin, *Proceedings of the Society for Experimental Biology and Medicine* 124 303 (1967).

Chlorphensin also was reported to inhibit allergen-reagin-induced histamine and SRS-A release from monkey lung tissue passively sensitized with human reagin, by Malley and Baecher *Journal of Immunology* 107 586 (1971).

Kimura, Inoue and Honda demonstrated that chlorphenesin and cromolyn sodium inhibited the degranulation of the rat mast cells mediated by IgE-anti-IgE reaction, and published their findings in *Immunology* 26 983 (1974).

Chlorphenesin also inhibited release of histamine induced by concanavalin A from basophil cells according to Siraganian and Siraganian, *Journal of Immunology* 112 2117 (1974).

Stites, Brecher, Schmidt and Berger showed that chlorphenesin inhibited mitogenic responses of mouse and human B and T cells induced by phytohemagglutinins, lipopolysaccharide or staphylococcal protein A. The compound also inhibited the mixed lymphocytes reactions in inbred strains of mice and in unrelated human (*Immunopharmacology* In Press (1979)).

These results suggest that chlorphenesin has a broad spectrum of effects on the inhibition of release of various mediator substances and that it can exert its effect without inducing tolerance or affecting antigenic priming of immuno-competent cells. However chlorphenesin possesses only a low order of activity and is rapidly metabolized and broken down in the body rendering its use impractical. The interesting properties of chlorphenesin stimulated investigation of related compounds.

Inai, Okazaki, Shimada, Kagei and Bessho, U.S. Pat. No. 3,846,480 patented Nov. 5, 1974 describe chlorphenesin in succinate and its alkali metal salts, and indicated that these were much superior to chlorphenesin in their anaphylactic histamine release-preventive effect. These compounds are not being used therapeutically because of inadequate clinical and pharmacological potency.

Reisner, Ludwig, Fukui and Berger U.S. Pat. No. 3,879,544 patented Apr. 22, 1975 developed a group of new aryl thioalkanones having the formula:

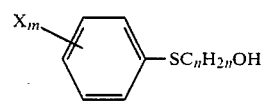

wherein X is halogen or lower alkyl; m is an integer 1 or 2 and n is an integer from 2 to 6, inclusive. As used throughout the instant specification and claims the term lower alkyl shall mean carbon chains containing 1–6 carbon atoms.

However, these compounds cause serious side effects, and have a high toxicity, and are therefore too dangerous to use.

As of 1975 and before, at the time of U.S. Pat. No. 3,879,544, and the early work on cromolyn sodium and chlorphenesin, it was thought that the symptoms of allergy were due primarily to the release of histamine. For this reason, compounds were only evaluated as to their ability to prevent release of histamine from sensitized cells. However, it is now recognized that symptoms of allergy are caused by the release of many other substances, including slow-reacting substance A(SRSA), serotonin, bradikinin, various prostaglandins, and many other mediators. Therefore the tests that were used were designed to enable one to determine whether the compounds of this invention suppress the release from cells and tissues not only of histamine but also of other mediator substances released during allergic reactions and tissue irritation. One of the substances having this property is compound 48/80, as stated by Goodman and Gillman, *The Pharmacological Basis of Therapeutics*, Third Edition, p 622, the Macmillan Company, New York (1965), now an accepted material in the test procedure described by Lewis and Whittle, *British Journal of Pharmacology* 61 229 (1977).

In work unrelated to allergic reactions, Berger and Fukui U.S. Pat. No. 3,549,766 patented Dec. 22, 1970 described a method of eliminating or reducing hypersensitivity to penicillin by administering in conjunction with the penicillin, certain phenoxy propanols or phenoxypropanediols having the structure:

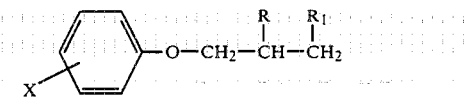

wherein X is selected from the group consisting of hydrogen, halogen, lower alkyl and lower alkoxy; and R and $R_1$ are each selected from the group consisting of hydrogen and hydroxyl, at least one being hydroxyl.

As used herein and the appended claims, the terms "lower alkyl" and "lower alkoxy" signify respectively alkyl and alkoxy radicals having from one to about six carbon atoms.

This group includes chlorphenesin, in the case when X is Cl and R and $R_1$ are each OH. Nothing in the patent suggests possible utility of phenoxy propanols or diols in inhibiting abnormal tissue reactivity due to specific allergic hypersensitivity or due to specific irritants by inhibiting the release of chemical mediators that are responsible for the symptoms of allergic diseases, and the many symptoms of irritation and inflammation produced by irritants and inflammation-causing substances.

In a contemporaneous paper, Berger and Fukui, *Giornale dell'Arteriosclerosi* V No. 5-Sept-Oct 1967 describe the effect of the phenoxy propanediols in decreasing the penicillin-induced passive anaphylaxis reaction, with particular emphasis on chlorphenesin, 3-p-chlorophenoxy, 1,2-propanediol. In the summary at the end of the paper, the authors comment:

> These observations appear to be of particular interest because the mode of action of these compounds appears to be entirely different from that of previously described inhibitors of anaphylactic reactions. The phenoxypropanediols do not destroy penicillin and do not affect its antibiotic action. They are devoid of antihistaminic and anti-inflammatory properties and do not act by depressing the general reactivity of the organism. The compounds appear to act by a selective blocking of certain antibody sites, thus making the antibody unable to react with penicillin. This effect is of particular interest because of its specificity. The action of phenoxypropanediols on cutaneous anaphylaxis may open up new approaches to the treatment of hypersensitivity and autoimmune diseases.

A corresponding report by Berger, Fukui, Ludwig, and Margolin appeared in *Proc. of the Society for Exp. Biology and Medicine* 124 303-310 (1967), and the same conclusion is reached at page 310.

In accordance with the present invention, a group of compounds are provided that are related to chlorphenesin but are far more effective in inhibiting mediator release, and are more resistant to inactivation by the metabolic reaction in the body. They are moreover free from toxic or deterious side effects. They are in fact from four to twenty times as effective, milligram for milligram, as chlorphenesin, and from five to fifty as effective, milligram for milligram, as cromolyn sodium, in suppressing the release of mediator substances. They consequently represent an important break-through in the treatment of allergic conditions, and for the first time permit a practical approach by way of inhibition of the release of all mediator substances.

The compounds in accordance with the invention are p-alkyl or cycloalkyl phenoxy alkanols and esters having the general formula:

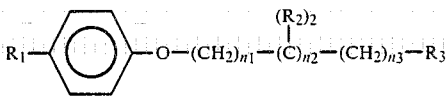

in which:
$R_1$ is an alkyl group having from one to six carbon atoms, preferably tertiary, and still more preferably tertiary-butyl; or a bivalent cycloalkylene group condensed with the phenyl ring at two positions, as in indane;

$R_2$ is lower alkyl having from one to three carbon atoms or hydrogen;

$R_3$ is hydroxyl or an ester group selected from the group consisting of $COOR_4$ and $OOCR_4$ derived from unsubstituted and hydroxy-substituted monocarboxylic acids and $COOR_5OOC$ and $OOCR_5COO$ derived from unsubstituted and hydroxy-substituted dicarboxylic acids, the acids being selected from the group consisting of aliphatic acids, including carbamic acid, having from one to about twelve carbon atoms; cycloaliphatic acids having from three to about twelve carbon atoms; carbocyclic aromatic acids having from six to about twenty carbon atoms; and nitrogen heterocyclic aromatic acids having from five to about twelve carbon atoms, $R_4$ being monovalent aliphatic, cycloaliphatic, aromatic, or nitrogen heterocyclic aromatic, and $R_5$ being divalent aliphatic, cycloaliphatic, aromatic, or nitrogen heterocyclic aromatic, the acids being esterified with aliphatic alcohols having from one to six carbon atoms; and carbonic acid monoalkyl esters, the alkyl having from one to three carbon atoms; and $n_1$, $n_2$ and $n_3$ represent the number of $CH_2$, $C(R_2)_2$ and $CH_2$ groups, respectively, and are numbers within the range from 0 to 10; and at least one of $n_1$, $n_2$ and $n_3$ is other than zero.

These compounds differs from the Reisner et al compounds disclosed in U.S. Pat. No. 3,879,544 in being oxy ethers rather than thio ethers. Moreover, in the series of the invention, the p-substituent on the phenoxy group is alkyl or cycloalkylene, and the alkyl, while it can be unbranched, is preferably tertiary, whereas Reisner et al disclosed no branched chain alkyl groups whatsoever. Replacement of thioether by oxyether eliminates the toxic reactions, which thus appear to be associated with the thio ether group, although this is not referred to in the Reisner et al patent.

These compounds inhibit abnormal tissue reactivity due to specific allergic hypersensitivity or due to specific irritants by inhibiting the release of chemical mediators that are responsible for the symptoms of allergic diseases, including allergic rhinitis, asthma, hypersensitivity of the skin and of the gastrointestinal canal, and the many symptoms of irritation and inflammation produced by irritants and inflammation-causing substances, and prevent rejection of transplanted cells and organs and particularly of bone marrow and insulin-producing Langerhans cells.

The compounds of this invention may also be used to prevent rejection of transplanted tissues and organs by decreasing and altering the graft versus host and host versus graft reactions. Examples of such a use would be transplantation of healthy bone marrow to patients suffering from leukemia, or transplantation of insulin-producing pancreatic Langerhans cells to diabetic patients.

The compounds of this invention also prevent the development of hypersensitivity to substances capable of producing allergic reactions on the skin or elsewhere when administered together with them.

The inhibiting effect of the compounds of the invention in all of the above types and classes of therapeutic effects is generically encompassed herein by the phrase:

"effective to inhibit abnormal tissue reactivity due to specific allergic hypersensitivity or due to specific irritants by inhibiting the release of chemical mediators that are responsible for the symptoms of allergic diseases and irritation and inflammation produced by irritants and inflammation-causing substances"

Exemplary $R_1$ alkyl substituents include methyl, ethyl, propyl, isopropyl, butyl, secondary-butyl, tertiary-butyl, amyl, secondary-amyl, tertiary-amyl, hexyl, secondary-hexyl, and tertiary-hexyl. Isobutyl has so far shown itself to be inactive, which is anomalous, and possibly incorrect.

Exemplary $R_1$ cyloalkylene substituents include cyclopropylene, cyclobutylene and cyclopentylene, forming five, six and seven membered carboxylic rings with the phenyl, as in indane and tetrahydroquinoline.

Exemplary $R_2$ are methyl, ethyl, propyl and isopropyl.

Exemplary $R_3$ are, in addition to hydroxy, ester groups $OOCR_4$ derived from monocarboxylic acids such as carbamic acid, acetic acid, propionic acid, butyric acid, valeric acid, hexoic acid, and hydroxy-substituted such monocarboxylic acids having a carbon:oxygen ratio from 1:1 to not exceeding 2:1, such as glycolic acid, and sugar acids such as glyceric acid, erythronic acid, threonic acid, gluconic acid, galactonic acid, mannonic acid, gluconic acid, idonic acid, attronic acid and allonic acid; cyclopropanoic acid, cylobutanoic acid, cyclopentanoic acid, cyclohexanoic acid, cycloheptanoic acid, cyclooctanoic acid, benzoic acid, salicylic acid, m-chlorobenzoic acid, p-chlorobenzoic acid, m-hydroxybenzoic acid, protocatechinic acid, gentisic acid, gallic acid, phenylacetic acid, toluic acids, xylic acids, hydrocinnamic acid, naphthoic acid, α-picolinic acid, isonicotinic acid, nicotinic acid, quinnic acid, quinaldinic acid, cinchroninic acid, acridine monocarboxylic acid, phenanthridine monocarboxylic acid, pyrimidine monocarboxylic acid, pyrazine monocarboxylic acid, pyridazine monocarboxylic acid, triazine monocarboxylic acid; methyl carbonic acid, and ethyl carbonic acid; and ester groups $COOR_4$ derived from alcohols and phenols such as methanol, ethanol, propanol, butanol, pentanol, hexanol, phenol, and benzyl alcohol; ester groups $OOCR_5COO$ derived from dicarboxylic acids such as oxalic acid, malonic acid, succinic acid, glutaric acid, adipic acid, pimelic acid, suberic acid, azelaic acid, and sebacic acid; and hydroxy-substituted dicarboxylic acids in a carbon:oxygen ratio from 1:1 to not exceeding 2:1, such as malic acid, tetrahydroxy adipic acid, mannosaccharic acid, idesaccharic acid, talomucic acid, tartaric acid, trihydroxy glutaric acid, glucuronic acid, galactouronic acid, saccharic acid and mucic acid.

In the preferred compounds, $n_1$ is a number from 3 to 8, and $n_2$ and $n_3$ are zero, $R_3$ is nicotinic acid, and $R_1$ is tertiary-butyl, tertiary-amyl, or tertiary-hexyl.

A number of preferred compounds falling within the invention are illustrated in Tables I and II.

The compounds of the invention can be made by any of three general syntheses:

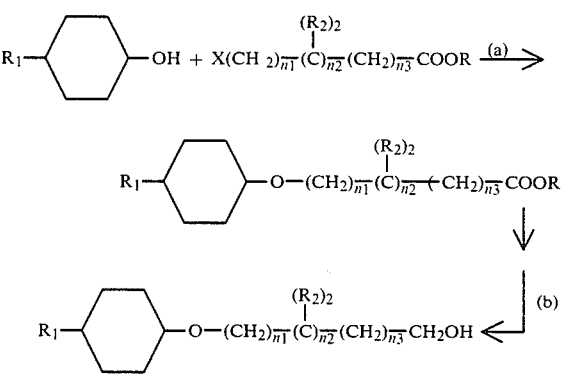

This is the procedure used in Examples I, III, VI, VII, and IX to XIV.

This route involves in step (a) reaction of a phenol having the $R_1$ substituent of Formula I, page 7, with an ester or acid corresponding in structure to the

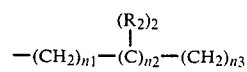

substituent, having a group X that is suitably activated for displacement by a phenoxide ion at the position where the group is to be linked to the phenolic hydroxy group. The reaction requires ionization of the phenolic substrate with a suitable base, such as an alkali metal hydride, an alkali metal hydroxide, carbonate or alkoxide, or an organic base such as a tertiary amine, for instance, triethyl amine, pyridine, or a quaternary ammonium hydroxide such as tetramethyl ammonium hydroxide, in an inert organic solvent, such as a polar solvent. Typical solvents are illustrated in the Examples applying this reaction, which follow.

The reaction proceeds at room temperature up to a moderately elevated temperature within the range from about 25° to about 150° C.

The COOR group is an ester derived from the acid COOH esterified with an alcohol, such as the alkanols, in which case R is an alkyl group, such as methyl, ethyl, propyl and butyl; an aryl group derived from a phenol, such as phenyl and naphthyl; an alkaryl group derived from an aryl alcohol, such as benzyl and phenethyl; and a cycloalkyl group derived from a cycloalkanol, such as cyclohexyl and cycloheptyl.

X represents the activated substituent, and is preferably halogen selected from the group consisting of chlorine, bromine and iodine, but sulfonyloxy groups can also be used.

The $n_1$, $n_2$ and $n_3$ substituents correspond of course to the like substituents of Formula I on page 7, as also does the $R_1$ substituent on the phenol.

If the desired compound of Formula I has as $R_3$ an ester group COOR, then step (b) of the reaction can be omitted. If the terminal group including $R_3$ has the structure $CH_2OH$ or $CH_2OOCR$, the step (b) is used.

In step (b) of this reaction, the phenoxy alkylene ester is reduced with a metal hydride, such as lithium aluminum hydride, diisobutyl aluminum hydride, or other hydrides, or a borane, converting the ester COOR group to a $CH_2OH$ group, in the presence of an inert organic solvent that is compatible with and inert to strong reducing agents. Ethers, such as diethyl ether, tetrahydrofuran, dioxane, and dimethoxyethane can be used, as well as hydrocarbons such as toluene, which may be favored with the alkyl metal hydrides.

Then, if the terminal $R_3$ group is to be $CH_2OOCR$, the $CH_2OH$ group is esterified with an acid RCOOH using conventional esterification procedures.

Syntheses B:

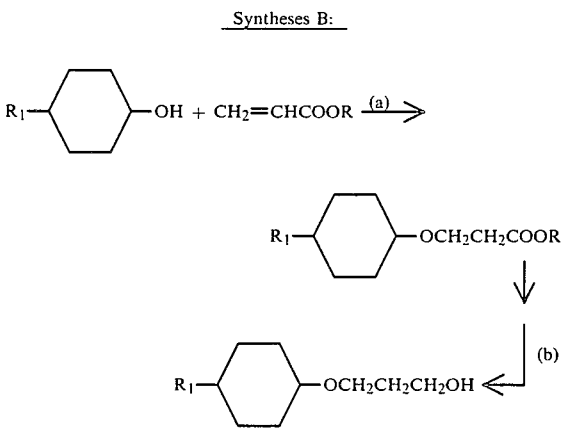

This is the procedure used in Examples II, and XVII to XXII.

In step (a) of this procedure, a phenol

having a para substituent corresponding to $R_1$ is employed together with a lower acrylic acid ester, which following reduction in step (b) produces a substituent corresponding to the

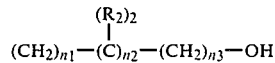

substituent of Formula I on page 7.

The reaction between the phenol and the lower acrylate ester requires ionization of the phenolic substrate with a suitable base, such as a metal hydride, alkali metal hydroxide, carbonate, or alkoxide, or a suitable organic base, as in Synthesis A, but it can also be carried out with only a catalytic quantity of the base, and in the absence of an inert organic solvent. The R substituent on the acrylic acid can be alkyl, aryl, alkaryl or cycloalkyl, but in this case better yields are obtained when R is of a higher molecular weight than methyl or ethyl, such as, for example, butyl.

The higher acrylate esters have higher boiling points, and it is likely, if the reaction is carried out under reflux, that the higher boiling point of the acrylate ester influences the reaction, with the best yields being obtained when the acrylate ester has a boiling point above 100° C.

If the desired compound of Formula I has as $R_3$ an ester group COOR, then step (b) of the reaction can be omitted. If the terminal group including $R_3$ has the structure $CH_2OH$ or $CH_2OOCR$, the step (b) is used.

In step (b) of this reaction, the COOR ester group is reduced to $CH_2OH$, as in Synthesis A, and a similar procedure can be used.

Then, if the terminal $R_3$ group is to be $CH_2OOCR$, the $CH_2OH$ group is esterififed with an acid RCOOH using conventionl esterification procedures.

Synthesis C:

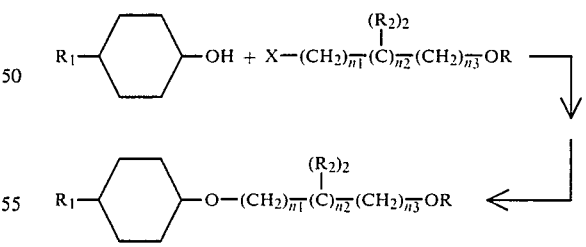

This synthesis also requires ionization of the phenolic substrate with a suitable base, preferably in an inert organic solvent as in Synthesis A, followed by alkylation with a suitable halogen-substituted or sulfonate ester-substituted alcohol or ester having a structure corresponding to the

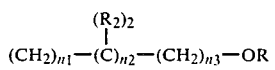

group, where OR is $R_3$ of Formula I on page 7.

The X group is suitably activated for displacement by a phenoxide ion, and can be any of the X groups of the esters in Synthesis A.

In the case where the alkylene substituent has two, four and five carbon atoms, $R_3$ is preferably an ester group, but in other cases $R_3$ can be either hydrogen or an ester group. At the particular chain length where the substituent has two, four and five carbon atoms, the cyclization of the reagent to ethylene oxide, tetrahydrofuran or tetrahydropyran is competitive with alkylation of the phenoxide, reducing the yield, unless the hydroxyl group is protected by esterification. Thus, when the number of carbon atoms in the substituent is two, four or five, the hydroxyl group should be protected by reaction with an acid, so as to form an ester, such as the acetate or propionate, the esterifying radical being removed, if the corresponding alkanol is required, by ordinary saponification following the alkylation. Where an ester is the desired reaction product, of course the ester moiety can be employed as the reagent.

This reaction proceeds at an elevated temperature within the range from about 25° to about 150° C., and is preferably carried out in an inert organic solvent, preferably a polar solvent.

This synthesis is used in Examples V and XVI.

In all of the Examples the calculated and found values are percent by weight.

EXAMPLE I

Preparation of 2-p-t-butylphenoxyethanol

A solution of 10.0 g (66.7 mmoles)p-tertibutylphenol in 50 ml dry dimethyl formamide was added, dropwise, to a mechanically stirred slurry of 8.4 g sodium hydride (as 50% oil dispersion)in 500 ml dry dimethyl formamide. To the phenoxide solution was added, dropwise, a solution of 6.3 g(66.3 mmoles) chloroacetic acid in 50 ml dry dimethyl formamide. The reaction mixture was stirred at room temperature for tow hours. The reaction mixture was diluted with 200 ml diethyl ether and acidified with 3N hydrochloric acid. The aqueous layer was removed and washed with 200 ml diethyl ether. The organic layers were combined, dried (MgSO4) and evaporated to a white gummy residue which was dried in vacuo yielding p-t-butylphenoxyacetuc acid, 9.0 g (65%).

Analysis: NMR Spectrum (CDCl$_3$) δ 1.25 (s, 9 H, (CH$_3$)$_3$C—), 4.60

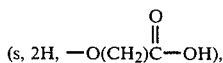
(s, 2H, —O(CH$_2$)C̈—OH), 7.03 (q, 4 H, —(C$_6$H$_4$)—).

To a stirred solution of 5.2 g (25 mmoles)2-p-tert-butylphenoxy)-acetic acid in 10 ml dry tetrahydrofuran cooled to 0° C. was added, dropwise, 45 ml(42 mmoles)0.95 M borane in tetrahydrofuran. After ten minutes at 0° C. the solution was stirred at room temperature for one hour. The reaction mixture was then acidified, pH=2, with 3 N hydrochloric acid, diluted with 50 ml water, and extracted with dichloromethane (2×200 ml). The organic layers were combined, dried and concentrated to a yellow oil which was distilled in vacuo (89° C./0.075 mm Hg) to a clear, colorless oil, 2-p-t-butylphenoxyethanol.

Analysis: NMR Spectrum (CDCl$_3$) δ 1.28 (s, 9 H, (CH$_3$)$_3$C—), 4.00 (m, 4 H, O-(CH$_2$CH$_2$)—OH), 7.10 (q, 4 H, —C$_6$H$_4$—).

Calculated: C$_{12}$H$_{18}$O$_2$: C, 74.2; H,9.34.

Found C, 74.4; H, 9.59.

EXAMPLE II

Preparation of 3-p-t-butyl-phenoxypropanol

A solution of 25 g (0.167 mole) p-tert-butylphenol, 0.2 g sodium hydride (as 50% dispersion in oil), 0.2 g N-phenyl-2-naphthylamine (as basic polymerization inhibitor) in 75.0 g (0.586 mole ) butyl acrylate was heated at 125° C. for four hours. The temperature was then reduced in 100° C. and the excess acrylate distilled under gentle vacuum. The resulting oil was filtered through 900 g silica gel (90 to 200 mesh) using chloroform as eluant to yield 21.0 g pure butyl 3-(p-tert-butylphenoxy)-propionate (45%).

This ester 21.0 g was dissolved in 500 ml dry ether and cooled to −5° C. in an ice/acetone bath. To the cold solution was added, cautiously, a slurry of 3.5 g lithium aluminum hydride in 100 ml dry ether. After one hour the excess lithium aluminum hydride was destroyed by the cautious addition of 200 ml ethyl acetate, then 50 ml water. The solution was filtered and the filtate partitioned between 200 ml ether - 200 ml water. The organic layer was removed, dried, and evaporated to a yellow oil which was vacuum distilled (116° C./0.35 mm) over potassium carbonate to a clear colorless oil, 3-p-t-butylphenoxypropanol, 10.1 g (64%).

Analysis: NMR Spectrum (CDCl$_3$) δ 1.31 (s, 9 H, (CH$_3$)$_3$—), 1.95 (m, 2 H,—CH$_2$ (CH$_2$)CH$_2$OH), 3.68 (t, 2 H, —CH$_2$(CH$_2$)OH), 3.95 (t, 2 H, —O(CH$_2$)CH$_2$ CHOH), 7.05 (q, 4 H, —(CH$_6$H$_4$)—).

Calculated: C$_{13}$H$_{20}$O$_2$: C, 75.0; H, 9.68.

Found: C, 75.2; H, 9.77.

EXAMPLE III

Preparation of 4-p-t-butylphenoxy-1-butanol

Method A. To a stirred slurry of 1.6 g sodium hydride (as 50% dispersion in oil) in 50 ml dry dimethyl formamide was added, dropwise, a solution of 5.0 g p-tert-butylphenol (33.3 mmoles) in 50 ml dry diemthyl formamide and the solution stirred under nitrogen until the phenoxide had totally formed. To the phenoxide was added a solution of 5.0 g 4-chlorobutyl acetate (33.3 mmoles) in 50 ml dry dimethyl formamide and the solution was stirred for fourteen hours. The reaction mixture was partitioned between water/ toluene. The organic layer was removed, washed with water, then 1 N sodium bicarbonate. The organic layer was removed, dried and evaporated to an orange oil, 5.6g. The oil was chromatographed on 500 g, 90 to 200 mesh silica gel (CH$_2$Cl$_2$ eluent) yielding pure 4-(p-tert-butylphenoxy)-butyl acetate.

Analysis: NMR Spectrum (CDCl$_3$) δ 1.3 (s, 9 H, (CH$_3$)$_3$C—), 2.00 (s,3 H, (s, 3H, CH$_3$)$_7$ 4.40

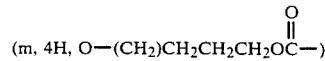
(m, 4H, O—(CH$_2$)CH$_2$CH$_2$CH$_2$OC̈—)

7.03 (q,4H, —(C$_6$H$_4$)—).

Calculated C$_{16}$H$_{24}$O$_3$; C, 72.7; H, 9.15.

Found: C, 73.0; H, 9.16.

Method B. To a stirred solution of 1.1 g, 14.0 mmoles acetyl chloride in 50 ml dry dichloromethane was added, dropwise, a solution of 2.0 g, 9.0 mmoles, of the alcohol 4-p-t-butylphenoxy-1-butanol, in 25 ml of dry dichloromethane. The solution was stirred for sixteen hours, then quenched with 50 ml water. The organic layer was removed, dried (MgSO4) and condensed to a yellow oil which was vacuum distilled (122° C./0.35 mm Hg) over potassium carbonate to a clear, colorless oil, 4-(p-tertbutylphenoxy)-butyl acetate. The NMR spectrum was in agreement with the NMR spectrum of the acetate ester prepared by Method A.

The acetate ester (24.9 g) was treated with 125 ml, 1 N methanolic potassium hydroxide at reflux for one hour. The methanol was then evaporated and the residue partitioned between 300 ml dichloromethane and 300 ml water. The dichloromethane solution was removed, dried (MgSO4), and evaporated to a yellow oil which was vacuum distilled (117° C., 0.8 mm) to a clear, colorless oil, 4-p-t-butylphenoxy-1-butanol, 19.2 g (92%).

Analysis: NMR Spectrum (CDCl3) δ 1.27 (s, 9 H, (CH3)3C—), 3.65 (t, 2 H,—(CH2)OH), 3.95 (t,2H, O(CH2)CH2—), 7.05 (q, 4 H, —(C6H4)—).

Calculated: $C_{14}H_{22}O_2$; C, 75.6; H, 9.97.
Found: C, 75.6; H, 10.0.

EXAMPLE IV

Preparation of 5-p-t-butylphenoxy-1-pentanol

To a stirred slurry of 3.2 g sodium hydride (as 50% dispersion in oil) in 100 ml dry dimethyl formamide was added, dropwise, a solution of 10.0 g (66.6 mmoles) p-tert-butylphenol in 100 ml dry dimethyl formamide and the solution stirred under nitrogen until the phenoxide had totally formed. To the phenoxide solution was added a solution of 12.0 g, 0.805 mole, 5-bromo-1-pentene in 100 ml dry dimethyl formamide. The reaction mixture was stirred for one hour then partitioned between 500 ml ether - 500 ml water. The ether was removed, dried (MgSO4), and evaporated to a yellow oil which was vacuum distilled (69° C./0.03 mm) to a clear, colorless oil 5-p-t-butylphenoxy-1-pentene, 10.5 g (72.2%).

Analysis: NMR Spectrum (CDCl3) δ 1.27 (s, 9 H, (CH3)3C—), 3.92 (t, 2 H, —O(CH2), 5.87 (m, 1 H, —(CH)=CH2), 7.04 (q, 4 H, —C6H4)—).

The 5-(p-tert-butylphenoxy)-1-pentene (10.5 g) was treated with 115 ml 0.5 M 9-borabicyclononane in tetrahydrofuran and the reaction mixture was stirred at reflux for one hour. The solution was cooled to room temperature and treated with 25 ml 3 N sodium hydroxide, then 10 ml 30% hydrogen peroxide. After the bubbling ceased the reaction mixture was partitioned between 150 ml ether -150 ml water. The ether layer ws removed, dried (MgSO4), and evaporated to a yellow oil which was chromatographed through 300 g, 90 to 200 mesh silica gel (2% MeOH/CH2Cl2 eluent) yielding a yellow oil which was vacuum distilled (126° C./0.75 mm) to a clear, colorless oil, 5-p-t-butylphenoxy-1-pentanol, 1.7 g.

Analysis: NMR Spectrum (CDCl3) δ 1.27 (s, 9 H, (CH3)3C—), 3.63 (t, 2 H,—(CH2)OH), 3.93 (t, 2 H, —(CH2)OAn), 7.08 (q, 4 H, —(C6H4)—.

Calculated: $C_{15}H_{24}O_2$; C, 76.2; H, 10.2.
Found: C, 76.2; H, 10.3.

EXAMPLE V

Preparation of 6-p-t-butylphenoxy-1-hexanol

To a stirred slurry of 0.64 g sodium hydride (as 50% dispersion in oil) in 10 ml dry dimethyl formamide was added, dropwise, a solution of 2.0 g (13.3 mmoles) p-tert-butylphenol in 10 ml dry dimethyl formamide. After the phenoxide had totally formed a solution of 1.8 g (13.1 mmoles) 6-chloro-1-hexanol in 10 ml dry dimethyl formamide was added and the mixture stirred for forty-eight hours. The reaction mixture was partitioned between 100 ml ether - 100 ml water. The ether was removed dried (MgSO4), and evaporated to an orange oil. The oil was chromatographed on 200 g 90 to 200 mesh silica gel (2% MeOH/CH2Cl2 eluent) to a yellow oil which ws vacuum distilled (136° C./0.25 mm) to afford 0.96 g 6-p-t-butylphenoxy-1-hexanol.

Analysis: NMR Spectrum (CDCl3) δ 1.30 (s, 9 H, (CH3)3C—), 3.58 (t, 2 H, —(CH2)OH), 3.91 (5, 2 H, —O(CH2)—CH2—), 7.05 (q, 4 H, —(C6H4)—).

Calculated: $C_{16}H_{26}O_2$:C, 76.8; H, 10.5.
Found: C, 76.8; H, 10.4.

EXAMPLE VI

Preparation of 8-p-t-butylphenoxy-1-octanol

Methyl 8-bromooctanoate was prepared by treating 8-bromooctanoic acid with excess thionyl chloride at reflux for two hours. Evaporation of the excess thionyl chloride and treatment of the acid chloride with excess methanol yielded the methyl 8-bromooctanoate as a yellow oil. To a stirred slurry of 0.64 g sodium hydride (as 50% dispersion in oil) in 10 ml dry dimethyl formamide was added, dropwise, a solution of 2.0 g, 13.1 mmoles, p-tert-butylphenol in 10 ml dry dimethyl formamide. After the phenoxide had totally formed, a solution of 3.2 g (13.3 mmoles), methyl 8-bromooctanoate, in 10 ml dry dimethyl formamide was added. The reaction mixture was stirred at room temperature for sixteen hours then partitioned between 100 ml hexane - 100 ml water. The organic layer was removed, dried (MgSO4), and condensed to a yellow oil, methyl 8-p-t-butylphenoxyoctanoate, 3.6 g.

Analysis: NMR Spectrum (CDCl3) δ 2.28 (t, 2 H, —(CH2)-13 COOCH3), 3.63

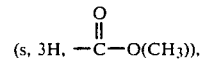
(s, 3H, —C—O(CH3)), 3.90 (t, 2 H, O—(CH2)—CH2—), 7.05 (q, 4 H, —C6H4)—).

The ester methyl 8-p-t-butylphenoxyoctanoate, 3,6 g, was dissolved in 100 ml dry diethyl ether and added, dropwise, to a stirred slurry of 0.4 g lithium aluminum hydride in 200 ml dry diethyl ether. After two hours the excess lithium aluminum hydride was quenched with 100 ml distilled water. The mixture was filtered through Celite. The organic layer was removed from the filtrate, dried (MgSO4), and condensed to a yellow oil, 0.9 g, which was vacuum distilled (155° C./0.2 mm) to a clear colorless oil, 8-p-t-butylphenoxy-1-octanol, 0.7 g.

Analysis: NMR Spectrum (CDCl3) δ 3.57 (t, 2 H, —(CH2)OH), 3.91 (t,2 H, —O—(CH2)CH2), 7.05 (q, 4 H, —(C6H4)—).

Calculated: $C_{18}H_{30}O_2$C, 77.7; H, 10.9.
Found: C, 77.5; H, 10.8.

EXAMPLE VII

Preparation of 11-t-butylphenoxy-1-undecanol 12.0 g, 48.2 mmoles, 11-bromoundecanoic acid was treated with excess thionyl chloride for two hours at reflux. The excess thionyl chloride was distilled off. The resulting residue dissolved in dichloromethane and treated with excess methanol. Evaporation yielded methyl 11-bromoundecanoate as an orange oil, 12.1 g. To a stirred slurry of 0.64 g sodium hydride (as 50% dispersion in oil) in 10 ml dry dimethyl formamide was added, dropwise, a solution of 2.0 g, (13.3 mmoles),p-tert-butylphenol in 10 ml dry dimethyl formamide. After the phenoxide had totally formed, a solution of 3.7 g, (13.3 mmoles), of methyl 11-bromoundecanoate in 10 ml dry dimethyl formamide was added and the solution stirred at room temperature under nitrogen for fourteen hours. The reaction mixture was then partitioned between 100 ml hexane - 100 ml water. The organic layer was removed, dried (MgSO4), and condensed to a yelldow oil, methyl 11-p-t-butylphenoxyundecanoate, 3.7 g.

The methyl 11-(p-tert-butylphenoxy)-undecanoate, 3,7 g, 10.6 mmoles, was dissolved in 100 ml dry diethyl ether and added, dropwise, to a stirred slurry of 0.5 g lithium aluminum hydride in 100 ml dry diethyl ether. After one hour the reaction mixture was filtered through Celite and the filtrate was treated with 100 ml 1 N hydrochloric acid. The organic layer was removed, dried (MgSO4), and concentrated to a yellow oil, 2.7 g. The oil was chromatographed on 200 g 90 to 200 mesh silica gel (2% MeOH/CH2Cl2 eluent) collecting the product as a white, waxy solid. The solid was recrystalized from warm pentane yielding pure 11-(p-tert-butylphenoxy)-undecanol, 1.1 g, m.p. 39° to 40° C.

Analysis: NMR Spectrum (CDCl3) δ 3.57 (t, 2 H, —(CH2)OH), 3.89 (t, 2 H, —O—(CH2)—CH2—), 7.05 (q, 4 H, —(C6H4)—).

Calculated: C21H36O2: C, 78.7; H, 11.3.
Found: C, 78.6; H, 11.3.

EXAMPLE VIII

Preparation of 5-p-t-butylphenylpentanol

Methyl 4-crotonyltriphenyl phosphonium bromide 9.2 g (20.9 mmoles) was dissolved in 500 ml ice water and carefully neutralized with 2% sodium hydroxide. The resulting precipitate was filtered and dried in vacuo yielding 6.8 g of the phosphorane. The phosphorane, 6.8 g (18.8 mmoles) was suspended in 100 ml methanol and to this was added 3.0 g (18.9 mmoles), p-tert-butylbenzaldehyde and the mixture was stirred at room temperature for one hour, then at 0° C. for sixteen hours. The product was collected by filtration to afford 1.4 g methyl 5-p-t-butylphenyl-2,4-pentadienoate.

Analysis: NMR Spectrum (CDCl3) δ 1.33 (s, 9 H, (CH3)3C—), 3.72

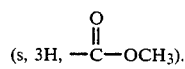
(s, 3H, —C—OCH3).

The olefin,methyl 5-p-t-butylphenyl-2,4-pentadienoate, 1,4 g, was dissolved in 50 ml methanol and hydrogenated at 1 atmosphere over 5% rhodium on alumina. The reaction mixture was then filtered through Celite and the filtrate evaporated to a yellow oil, methyl 5p-t-butylphenylpentanoate, 1.4 g.

Analysis: NMR Spectrum (CDCl3) δ 1.30 (s, 9 H, (CH3)3C—), 2.45

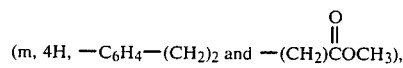
(m, 4H, —C6H4—(CH2)2 and —(CH2)COCH3), 3.61

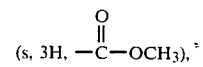
(s, 3H, —C—OCH3), 7.18 (q, 4 H,—C6H4—).

The ester methyl 5-p-t-butylphenylpentanoate 1.4 g was dissolved in 50 ml anhydrous ether and added, dropwise, to an ice cold slurry of 200 mg lithium aluminum hydride in 50 ml anhydrous ether. After one hour the solution was filtered through Celite and the filtrate was washed with 200 ml 1 N hydrochloric acid. The organic layer was removed, dried (MgSO4) and concentrated to a yellow oil which was vacuum distilled (134° C./0.75 mm) to a clear, colorless oil 5-p-t-butylphenylpentanol, 0.34 g.

Analysis: NMR Spectrum (CDCl3)δ1.32 (s,9H, (CH3)3C-), 2.58 (t,2H,—C6H4—(CH2)—), 3.59 (t,2H,—(CH2)OH), 7.18 (q,4H,—C6H4—).

Calculated: C15H24O: C,81.8;H,11.0.
Found: C,81.0;H,10.8.

EXAMPLE IX

Preparation of 4-p-t-butylphenoxy-1-butyl benzoate

To a well stirred solution of 2.0 g, 9.0 mmoles, of the alcohol 4-p-t-butylphenoxy-1-butanol, and 1.25 ml pyridine in 30 ml benzene was added, 1.8 g, 13.4 mmoles, benzoyl chloride in 30 ml benzene, and the solution stirred under nitrogen for sixteen hours. The reaction mixture was then filtered and the filtrate washed with 50 ml 1 N hydrochloric acid. The organic layer was removed, dried (MgSO4) and evaporated to a yellow oil which was vacuum distilled (168° C./0.4 mm) to a clear, colorless oil, 4-p-t-butylphenoxy-1-butyl benzoate, 1.6 g.

Analysis: NMR Spectrum (CDCl3)δ1.28 (s,9H, (CH3)3C—), 1.95 (m,4H,OCH2 (CH2CH2)CH2O), 4.00

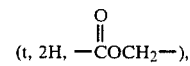
(t, 2H, —COCH2—), 4.40 (t,2H,—C6H4O(CH2)—), 7.05 (q,4H, —C6H4—), 7.53 (m,3H, benzoyl 3,4,5-H's) 8.08 (m,2H, benzoyl 2,6-H's).

Calculated: C21H26O3: C, 77.3,H, 8.03.
Found: C,76.9; H,7.99.

EXAMPLE X

Preparation of methyl 4-p-t-butylphenoxy-1-butylcarbonate

To a well stirred solution of 2.0 g, 9.0 mmoles, of the alcohol 4-p-t-butylphenoxy-1-butanol, and 0.8 ml pyridine in 25 ml dichloromethane was added 1.6 g (16.8 mmoles) methyl chloroformate in 25 ml dichloromethane and the solution was stirred for forty-eight hours. The reaction mixture was then evaporated and the residue chromatographed on 200 g 90 to 200 mesh silica gel (chloroform eluent) yielding 2.8 g of pale yellow oil. Vacuum distillation (131° C./0.25 mm) rendered the product as a clear, colorless oil, methyl 4-p-t-butyl-phenoxy-1-butylcarbonate, 1.5 g.

Analysis: NMR Spectrum (CDCl₃)δ1.26 (s,9H, (CH₃)₃C—), 1.82 (m,4H,OCH₂ (CH₂CH₂)CH₂O),3.73 (s,3H,CO(CH₃)), 8.93

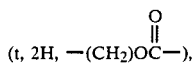

4.18 (t,2H,—C₆H₄O(CH₂)—), 7.05 (q,4H,—C₆H₄—).
Calculated: C₁₆H₂₄O₄: C, 68.5; H, 8.63.
Found: C, 69.3; H, 8.73.

EXAMPLE XI

Preparation of 4-p-t-butylphenoxy-1-butyl nicotinate

Nicotinoyl chloride was prepared by treating 100 g (0.81 mole) of nicotinic acid with 280 ml of thionyl chloride at reflux for two hours. The excess thionyl chloride was removed in vacuo and the crystalline acid chloride hydrochloride was suspended in 500 ml of dichloromethane. To the stirred mixture was added 66 g (0.30 mole) of 4-p-t-butylphenoxy-1-butanol dissolved in 400 ml of dichloromethane. After forty-eight hours the mixture was washed with one liter of saturated sodium bicarbonate. The dichloromethane solution was dried over magnesium sulfate and evaporated to a syrupy residue. The material was chromatographed on 1 kg of silica gel with elution by dichloromethanemethanol, 96:4, to afford 43.8 g (45%) of the nicotinate ester as an oil. The hydrobromide salt was prepared by treatment of a solution of 43.8 g in 800 ml of ethyl acetate with 30 ml of 4.5 N hydrogen bromide in ether. The precipitate was collected, washed with pentane and dried, m.p. 132°–133° C.

Analysis: 15 NMR Spectrum (d₆DMSO)δ1.30 (s,9H, (CH₃)₃C—), 1.96 (m,4H,OCH₂(CH₂CH₂)CH₂O), 4.05

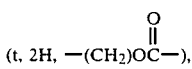

4.49 (t,2H,O (CH₂)—CH₂—), 7.09 (q,4H,—C₆H₄), 8.14 (q,1H,Pyr—5H), 9.01 (q,2H,Pyr—4,6-H's), 9.34 (s,1H,Pyr—2H).
Calculated: C₂₀H₂₅NO₃.HBr: C, 58.8; H, 6.42; N, 3.43.
Found: C, 59.0; H, 6.43; N, 3.33.

EXAMPLE XII

Preparation of 3-p-t-butylphenoxypropanol carbamate

To a stirred slurry of 3.0 g, 14.4 mmoles, of the alcohol 3-p-t-butylphenoxy propanol, and 2.5 g potassium cyanate in 50 ml benzene was added 3.4 g trifluoroacetic acid and the solution was stirred under nitrogen for two hours. The mixture was then treated with 50 ml water. The organic layer was removed, dried (MgSO₄), and condensed to an orange oil. The oil was dissolved in 25 ml pentane and stored at 0° C. The crystals were filtered and dried in vacuo yielding 0.9 g of the urethane, m.p. 84° to 85° C.

Analysis: NMR Spectrum (CDCl₃)δ1.32 (s,9H, (CH₃)₃C—), 2.08 (m,2H,O—CH₂(CH₂)CH₂O—), 4.02

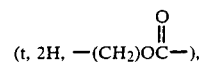

4.24 (t,2H,—O(CH₂)CH₂—), 7.05 (q,4H,—C₆H₄—).
Calculated: C₁₅H₂₁NO₃: C, 66.9; H, 8.42; N, 5.57.
Found: C, 66.9; H, 8.20; N, 5.51.

EXAMPLE XIII

Preparation of 2-methyl-4-p-t-butylphenoxy-2-butanol

To a solution of freshly prepared methyl magnesium iodide (from 144 g, 1.01 moles, methyl iodide and 54 g, 2.25 moles, magnesium in 700 ml dry diethyl ether) was added a solution of 10.0 g (36.0 mmoles) of the ester butyl 3-p-t-butylphenoxy propionate in 200 ml diethyl ether. After one hour the reaction mixture was poured over ice/20% H₂SO₄. The yellow organic layer was dried and evaporated. The resulting dark oil was chromatographed on 500 g 90 to 200 mesh silica gel (dichloromethane eluent) yielding an oil which was vacuum distilled (110° C./0.15 mm) to a yellow viscous oil which solidified on cooling, 2-methyl-4-p-t-butylphenoxy-2-butanol, 3.1 g.

Analysis: NMR Spectrum (CDCl₃)δ1.27 (s,15H, (CH₃)₃C—,—C(CH₃)₂OH), 1.93

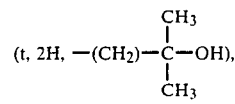

4.13 (t,2H,—O—(CH₂)—), 7.05 (q,4H,—C₆H₄—).
Calculated: C₁₅H₂₄O₂: C, 75.0; H, 10.0.
Found: C, 75.1; H, 10.1.

EXAMPLE XIV

Preparation of 3-p-t-butylphenoxypropyl nicotinate hydrochloride

Nicotinyl chloride was prepared by treating 3.0 g, 8.3 mmoles, nicotinic acid with 10.0 ml thionyl chloride at reflux for two hours. The excess thionyl chloride was distilled and the crystalline acid chloride suspended in 25 ml dichloromethane. To the stirred slurry was added, dropwise, a solution of 1.0 g (4.5 mmoles) of the alcohol 3-p-t-butylphenoxy propanol, in 25 ml dichloromethane. After thirty minutes the excess acid chloride was quenched, cautiously, with water. The organic layer was removed, dried (MgSO₄), and concentrated to an orange gum. This was dissolved in 25 ml methanol and treated with 10 ml 3% methanolic hydrogen chloride. The methanol was evaporated and the resulting white solid recrystallized from hot ethyl acetate yielding the product, 3-p-t-butylphenoxypropyl nicotinate hydrochloride, 0.4 g, as a white crystalline material, m.p. 134° to 136° C.

Analysis: Calculated: C₁₉H₂₃NO₃.HCl: C, 65.2; H, 6.92; N, 4.00. Found: C, 65.5; H, 6.89; N, 4.29.

EXAMPLE XV

Preparation of 3-p-n-propylphenoxy ethanol

To a well-stirred slurry of 3.9 g sodium hydride (as 50% dispersion in oil) in 300 ml dry dimethyl formamide was added, dropwise, a solution of 5.0 g, (36.7 mmoles) p-n-propylphenol in 125 ml dry dimethyl formamide. After the phenoxide had totally formed a solution of 3.5 g, 36.8 mmoles, chloroacetic acid in 50 ml dry dimethyl formamide was added and the solution was heated to 60° C. for 1.5 hours. The mixture was then partitioned between 200 ml toluene and 200 ml 3 N hydrochloric acid. The organic layer was removed, washed with water (3×200 ml), dried (MgSO$_4$) and concentrated to a pale yellow crystalline product. This crystalline material was dissolved in 25 ml ice cold dry tetrahydrofuran. To the cold solution was added, dropwise, 33 ml 0.94 molar borane in tetrahydrofuran. After two hours the excess borane was destroyed by careful addition of water. The solution was acidified with 3 N hydrochloric acid, diluted with 250 ml water, and extracted with 200 ml dichloromethane. The organic layer was removed, dried (MgSO$_4$), and evaporated to a yellow oil which was vacuum distilled (105° C./0.35 mm) to a clear, colorless oil, 3-p-n-propylphenoxy ethanol, 1.0 g.

Analysis: NMR Spectrum (CDCl$_3$)δ0.93 (t,3H, (CH$_3$)—CH$_2$—), 1.5 (m,2H, CH$_3$(CH$_2$)CH$_2$—), 2.52 (t,2H,—CH$_2$—(CH$_2$)—C$_6$H$_4$—), 3.90 (m,4H,—O—(CH$_2$—CH$_2$)OH), 6.93 (q,4H,—C$_6$H$_4$—).
Calculated: C$_{11}$H$_{16}$O$_2$: C, 73.3; H, 8.95
Found: C, 72.9; H, 9.18.

EXAMPLE XVI

Preparation of 4-p-n-propylphenoxy butanol

To a stirred slurry of 2.0 g sodium hydride (as 50% dispersion in oil) in 50 ml dry dimethyl formamide was added dropwise, a solution of 5.0 g (36.8 mmoles) p-n-propylphenol in 50 ml dry dimethyl formamide. After the phenoxide had totally formed a solution of 5.5 g (36.4 mmoles) 4-chlorobutyl acetate in 50 ml dry dimethyl formamide was added and the solution heated at 55° C. for sixteen hours. The mixture was then diluted with 1 liter water and extracted with 300 ml toluene. The toluene was removed, dried and evaporated to a yellow oil. This oil was treated with 75 ml 1 N methanolic potassium hydroxide at reflux for one hour. The methanol was then distilled and the residue partitioned between water/diethyl ether. The ether was separated, dried (MgSO$_4$) and concentrated to a yellow oil which was vacuum distilled (110° C./0.10 mm Hg) to a clear, colorless oil, 4-p-n-propylphenoxy butanol, 1.7 g.

Analysis: NMR Spectrum (CDCl$_3$)δ0.93 (t,3H, (CH$_3$)—CH$_2$—), 1.68 (m,6H, CH$_2$(CH$_2$CH$_2$)COH+CH$_3$(CH$_2$)CH$_2$—), 2.50 (t,2H,—(CH$_2$)—C$_6$H$_4$—), 3.64 (m,2H, CH$_2$—(CH$_2$)OH), 3.96 (t,2H,—C$_6$H$_4$—O(CH$_2$)—), 6.94 (q,4H,—C$_6$H$_4$—).
Calculated: C$_{13}$H$_{20}$O$_2$: C, 75.0; H, 9.68.
Found: C, 75.2; H, 9.72.

EXAMPLES XVII to XXIV

Synthesis of 3-(aryloxy)-propanols of Table A

A solution of 1 equivalent of the substituted phenol, 1 equivalent of sodium hydride, 2.5 equivalents of the acrylate ester and N-phenyl-2-naphthylamine (0.01 mole/1mole phenol) to act as basic polymerization inhibitor was heated under nitrogen to 115° C. for three hours. The temperature was then reduced to 65° C. and the excess acrylate removed under vacuum. The residue was chromatographed on 90 to 200 mesh silica gel yielding the pure 3-phenoxypropionate ester. The ester was dissolved in anhydrous ether and added, cautiously, to a stirred slurry of lithium aluminum hydride in anhydrous ether. After one hour the excess hydride was quenched with sodium sulfate decahydrate. The residue was partitioned between water/ethyl acetate. The organic layer was removed, dried (MgSO$_4$), and condensed to an oil which was vacuum distilled to the desired 3-(aryloxy) propanol.

By this procedure the following 3-(aryloxy) propanols were prepared:

TABLE A

| Example No. | R$_1$* | Boiling point | % Yield from Phenol | Formula | Theoretical % C | Theoretical % H | Actual % C | Actual % H |
|---|---|---|---|---|---|---|---|---|
| XVII 3-p-n-Propylphenoxy propanol | p-CH$_3$CH$_2$CH$_2$ | 119° C./0.15 mm Hg | 35.3 | C$_{12}$H$_{18}$O$_2$ | 74.2 | 9.34 | 73.9 | 9.38 |
| XVIII 3-p-i-Propylphenoxy propanol | p-(CH$_2$)$_2$CH— | 100° C./0.1 mm Hg | 17.1 | C$_{12}$H$_{18}$O$_2$ | 74.2 | 9.34 | 74.0 | 9.20 |
| XXIX 3-p-n-Pentylphenoxy propanol | p-CH$_3$CH$_2$CH$_2$CH$_2$CH$_2$— | 125° C./0.35 mm Hg | 6.5 | C$_{14}$H$_{22}$O$_2$ | 75.6 | 9.97 | 75.5 | 9.98 |
| XX 3-p-sec-Butylphenoxy propanol | p-CH$_3$CH$_2$CH(CH$_3$)— | 121° C./0.15 mm Hg | 34.6 | C$_{13}$H$_{20}$O$_2$ | 75.0 | 9.68 | 74.5 | 9.75 |
| XXI 3-p-i-Butylphenoxy propanol | p-(CH$_3$)$_2$CHCH$_2$— | 110° C./0.10 mm Hg | 23.7 | C$_{13}$H$_{20}$O$_2$ | 75.0 | 9.68 | 74.7 | 9.61 |
| XXII 3-m-i-Propylphenoxy propanol | m-(CH$_3$)$_2$CH— | 113° C./0.11 mm Hg | 34.7 | C$_{12}$H$_{18}$O$_2$ | 74.2 | 9.34 | 73.4 | 9.33 |
| XXIII 3-m-Br—Phenoxy propanol | m-Br | 118° C./0.15 mm Hg | 15.4 | C$_9$H$_{11}$O$_2$Br | 46.78 | 4.80 | | |
| XXIV 3-Indanoxy propanol | (indanyl-O—) | 125° C./0.10 mm Hg | 14.0 | C$_{12}$H$_{16}$O$_2$ | 74.97 | 8.39 | | |

*Formula of Table B

The following Table correlates the preceding Examples I to XXII with the formula on page 7:

TABLE B $$R_1-\bigcirc-O-(CH_2)_{n1}-(C)_{n2}-(CH_2)_{n3}-R_3$$
with $(R_2)_2$ on the central C

| Example No. | $R_1$ | $R_2$ | $R_3$ | $n_1$ | $n_2$ | $n_3$ |
|---|---|---|---|---|---|---|
| I | t-$C_4H_9$ | None | OH | 2 | 0 | 0 |
| II | t-$C_4H_9$ | None | OH | 3 | 0 | 0 |
| III | t-$C_4H_9$ | None | OH | 4 | 0 | 0 |
| IV | t-$C_4H_9$ | None | OH | 5 | 0 | 0 |
| V | t-$C_4H_9$ | None | OH | 6 | 0 | 0 |
| VI | t-$C_4H_9$ | None | OH | 8 | 0 | 0 |
| VII | t-$C_4H_9$ | None | OH | 11 | 0 | 0 |
| VIII* | t-$C_4H_9$ | None | OH | 5 | 0 | 0 |
| IX | t-$C_4H_9$ | None | O—C(=O)—$C_6H_5$ | 4 | 0 | 0 |
| X | t-$C_4H_9$ | None | O—C(=O)—O—$CH_3$ | 4 | 0 | 0 |
| XI | t-$C_4H_9$ | None | O—C(=O)—(pyridyl) | 4 | 0 | 0 |
| XII | t-$C_4H_9$ | None | O—C(=O)—$NH_2$ | 3 | 0 | 0 |
| XIII | t-$C_4H_9$ | $CH_3$ and H | OH | 2 | 1 | 0 |
| XIV | t-$C_4H_9$ | $CH_3$ and H | O—C(=O)—(pyridyl) | 3 | 0 | 0 |
| XV | n-$C_3H_7$ | $CH_3$ and H | OH | 2 | 0 | 0 |
| XVI | n-$C_3H_7$ | $CH_3$ and H | OH | 4 | 0 | 0 |
| XVII | n-$C_3H_7$ | $CH_3$ and H | OH | 3 | 0 | 0 |
| XVIII | iso-$C_3H_7$ | $CH_3$ and H | OH | 3 | 0 | 0 |
| XIX | n-$C_5H_{11}$ | $CH_3$ and H | OH | 3 | 0 | 0 |
| XX | sec-$C_4H_9$ | $CH_3$ and H | OH | 3 | 0 | 0 |
| XXI | iso-$C_4H_9$ | $CH_3$ and H | OH | 3 | 0 | 0 |
| XXII | iso-$C_3H_7$ (meta) | $CH_3$ and H | OH | 3 | 0 | 0 |
| XXIII | Br (meta) | None | OH | 3 | 0 | 0 |
| XXIV | indanyl (meta) | None | OH | 3 | 0 | 0 |

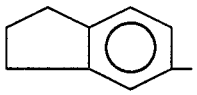

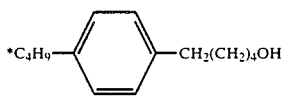

*$C_4H_9$—$C_6H_4$—$CH_2(CH_2)_4OH$

EXAMPLE XXV

Preparation of p-t-butylphenoxybutane:

To a stirred slurry of 4.2 g sodium hydride (as 50% dispersion in oil) in 50 ml dry dimethyl formamide was added, dropwise, a solution of 5.0 g (33.3 mmoles) p-t-butylphenol in 50 ml dry dimethyl formamide. After the phenoxide had totally formed a solution of 9.1 g (66.6 mmoles) n-butylbromide in 50 ml dry dimethyl formamide was added and the mixture stirred for sixteen hours. The reaction mixture was cautiously diluted with 200 ml water and extracted with hexane. The organic layer was removed, dried ($MgSO_4$) and concentrated to a yellow oil which was vacuum distilled (72°/0.8 mm) to a clear, colorless oil, 6.1 g, identified as p-t-butylphenoxybutane.

Analysis: NMR Spectrum ($CDCl_3$)$\delta$0.95 (t,3H, ($CH_3$)—$CH_2$—), 1.27 (s,9H, ($CH_3$)$_3$C—), 1.63 (m,4H,$OCH_3(CH_2CH_2)CH_3$), 3.93 (t,2H,O—($CH_2$)—), 7.07 (q,4H,—$C_6H_4$—).

Calculated: $C_{14}H_{22}O$: C, 81.5; H, 10.8.

Found: C, 81.7; H, 10.7.

EXAMPLE XXVI

Preparation of p-n-Propylphenoxybutane

To a stirred slurry of 4.2 g sodium hydride (as 50% dispersion in oil) in 50 ml dry dimethyl formamide was added, dropwise, a solution of 5.0 g (36.8 mmoles) p-n-propylphenol in 50 ml dry dimethyl formamide. After the phenoxide had totally formed a solution of 9.0 g (65.9 mmoles) n-butylbromide in 50 ml dry dimethyl formamide and the mixture stirred at room temperature for sixteen hours. The reaction mixture was cautiously diluted with 200 ml water and extracted with hexane. The organic layer was dried ($MgSO_4$) and concentrated to a yellow oil which was vacuum distilled (69°/0.225 mm) to a clear, colorless oil, 4.7 g identified as p-n-propylphenoxybutane.

Analysis: NMR Spectrum ($CDCl_3$)δ0.93 (m,H H, $(CH_3)CH_2CH_2$—+$(CH_3)CH_2CH_2CH_2$—), 1.57 (m,6H, $CH_3(CH_2CH_2)CH_2$—O+$CH_3(CH_2)CH_2$—$C_6H_4$—), 2.25 (t,2H,—$(CH_2)$—$C_6H_4$—), 3.91 (t,2H,—$O(CH_2)$—), 6.91 (q,4H,—$C_6H_4$—).

EXAMPLE XXVII

Preparation of 3-(p-chlorophenoxy)-lactic acid

A mixture of 1.8 g (14.7 mmoles)3-chlorolactic acid and 3.4 g p-chlorophenol in 15 ml 3.3 N sodium hydroxide was stirred under reflux for two hours. The mixture was cooled to room temperature and acidified to pH=3, with concentrated hydrochloric acid. The resulting white crystals were filtered and dissolved in hot water and the hot solution was adjusted to pH=1 with concentrated sulfuric acid. Upon cooling the product, 3-(p-chlorophenoxy)-lactic acid was collected as clear crystals, 0.7 g, m.p. 135° to 136° C.; Edelson, et al. *Biochem Pharmacol* 18, 2331 (1969) reported m.p. 137° to 138° C.

EXAMPLE XXVIII

Preparation of βmethoxy ethoxy methyl glycolate ester of 4-p-t-butylphenoxy-1-butanol To a solution of 9.0 g (0.1 mole) of methyl glycolate in 150 ml of acetonitrile is added 24.7 g (0.11 mole) of the triethyl ammonium salts of methoxy ethoxy methyl chloride and the mixture stirred at reflux for one hour. The solvent is removed in vacuo and the residue is treated with 200 ml of toluene. The insoluble salts are removed by filtration and 22.0 g (0.1 mole) of 4-p-t-butylphenoxy-1-butanol is added to the filtrate. After addition of 0.24 g (0.005 mole) of sodium hydride as a 50% oil dispersion, the mixture is heated to boiling and methanol fractionally distilled until transesterification is complete. The solvent is removed in vacuo and the product purified by chromatography on silica gel.

The effectiveness of the compounds of the invention in inhibiting the release of mediators from mast cells induced by administration of compound 48/80, was evaluated using the procedure described by Lewis and Whittle, *British Journal of Pharmacology* 61 229 (1977).

EXAMPLES 1 to 14

For purposes of comparision, fourteen compounds of the invention having the structure shown in Table I were evaluated against four test compounds including chlorphenesin and cromolyn sodium, as well as other structurally related compounds. The following results were obtained:

TABLE I $$R_1-\left[\text{phenyl}\right]-O-(CH_2)_{n1}-(C)_{n2}-(CH_2)_{n3}-R_3 \quad (R_2)_2$$

| Example No. | $R_1$ | $-O-(CH_2)_{n1}-(C)_{n2}-(CH_2)_{n3}-R_3$ $(R_2)_2$ | Concentration inhibiting release 30% or more | Activity relative to chlorophenesin | Activity relative to cromolyn sodium |
| --- | --- | --- | --- | --- | --- |
| Control | | | | | |
| 1 | Chlorphenesin 4-chloro | —O—$CH_2$.CHOH—$CH_2OH$ | 100 | 1.0 | 2.5 |
| 2 | 4-chloro | —O—$CH_2$.CHOH.COOH | Inactive | 0 | 0 |
| 3 | 3-bromo | —O—$CH_2$.$CH_2$.$CH_2OH$ | Inactive | 0 | 0 |
| 4 | Cromolyn sodium | —O—$CH_2$.$CH_2$.$CH_2OH$ | 250 | 0.4 | 1.0 |
| Example | | | | | |
| 1 | 4-n-propyl | —O—$CH_2$.$CH_2OH$ | 75 | 1.3 | 3.3 |
| 2 | 4-tertiary-butyl | —O—$CH_2$.$CH_2OH$ | 50 | 2.0 | 5.0 |
| 3 | 3-isopropyl | —O—$CH_2$.$CH_2$.$CH_2OH$ | 75 | 1.3 | 3.3 |
| 4 | 4-isopropyl | —O—$CH_2$.$CH_2$.$CH_2OH$ | 25 | 4.0 | 10.0 |
| 5 | 4-n-propyl | —O—$CH_2$.$CH_2$.$CH_2OH$ | 25 | 4.0 | 10.0 |
| 6 | 4-isobutyl | —O—$CH_2$.$CH_2$.$CH_2OH$ | Inactive | 0 | 0 |
| 7 | 4-tertiary-butyl | —O—$CH_2$.$CH_2$.$CH_2OH$ | 10 | 10.0 | 25.0 |
| 8 | 4-sec-butyl | —O—$CH_2$.$CH_2$.$CH_2OH$ | 25 | 4.0 | 10.0 |
| 9 | 4-pentyl | —O—$CH_2$.$CH_2$.$CH_2OH$ | 25 | 4.0 | 10.0 |
| 10 | Cyclobutylene (Indane) | —O—$CH_2$.$CH_2$.$CH_2OH$ | 25 | 4.0 | 10.0 |
| 11 | 4-n-propyl | —O—$CH_2$.$CH_2$.$CH_2$.$CH_2OH$ | 25 | 4.0 | 10.0 |
| 12 | 4-tertiary-butyl | —O—$CH_2$.$CH_2$.$CH_2$.$CH_2OH$ | 10 | 10.0 | 25.0 |
| 13 | 4-n-propyl | —O—$CH_2$.$CH_2$.$CH_2$.$CH_3$ | 50 | 2.0 | 5.0 |
| 14 | 4-n-propyl | —O—$CH_2$.$CH_2$—$C(CH_3)_2OH$ | 50 | 2.0 | 5.0 |

The compounds of the invention were evaluated against cromolyn sodium and against chlorphenesin by assigning to these controls, respectively, an activity of one, and then representing the activity of the compound of the invention in comparison thereto as a multiple of one. It is apparent from the results in Table I that the compounds of the invention are many times more effective than either chlorphenesin or cromolyn sodium.

It is interesting to note that the 4-chloro and 3-bromo compounds of Controls 2 and 3 in contrast to chlorphenesin ary-butyl phenoxy ethers having various alkanol or alkanol ester ($R_3$) substituents, as noted in Table II.

These were tested by the Lewis and Whittle procedure, with the following results:

TABLE II

| Example No. | $R_1$ | $-O-(CH_2)_{n1}-(C)_{n2}-(CH_2)_{n3}-R_3$ <br> $(R_2)_2$ | Concentration inhibiting release 30% or more | Activity relative to chlorophenesin | Activity relative to cromolyn sodium |
|---|---|---|---|---|---|
| Example | | | | | |
| 15 | 4-t-$C_4H_9$ | $-O-CH_2.CH_2.OH$ | 50 | 2.0 | 5.0 |
| 16 | 4-t-$C_4H_9$ | $-O-CH_2.CH_2.CH_2.OH$ | 10 | 10.0 | 25.0 |
| 17 | 4-t-$C_4H_9$ | $-O-CH_2.CH_2.CH_2.CH_2.OH$ | 10 | 10.0 | 25.0 |
| 18 | 4-t-$C_4H_9$ | $-O-CH_2.CH_2.CH_2.CH_2.CH_2.OH$ | 10 | 10.0 | 25.0 |
| 19 | 4-t-$C_4H_9$ | $-O-(CH_2)_6OH$ | 5 | 20.0 | 50.0 |
| 20 | 4-t-$C_4H_9$ | $-O-(CH_2)_8OH$ | 5 | 20.0 | 50.0 |
| 21 | 4-t-$C_4H_9$ | $-O-(CH_2)_{11}OH$ | 150 | 0.7 | 1.7 |
| 22 | 4-t-$C_4H_9$ | $-O-CH_2.CH_2.C(CH_3)_2.OH$ | 25 | 4.0 | 10.0 |
| 23 | 4-t-$C_4H_9$ | $-O-CH_2.CH_2.CH_2-O-CONH_2$ | 10 | 10.0 | 25.0 |
| 24 | 4-t-$C_4H_9$ | $-O-(CH_3)_4-O-CO.CH_3$ | 10 | 10.0 | 25.0 |
| 25 | 4-t-$C_4H_9$ | $-O-(CH_2)_4-O-CO.O.CH_3$ | 15 | 6.7 | 16.7 |
| 26 | 4-t-$C_4H_9$ | 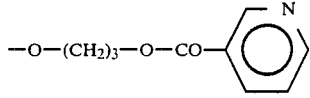 $-O-(CH_2)_3-O-CO-$ (3-pyridyl) | 10 | 10.0 | 25.0 |
| 27 | 4-t-$C_4H_9$ | 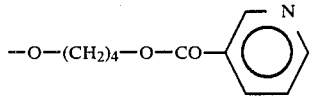 $-O-(CH_2)_4-O-CO-$ (3-pyridyl) | 5 | 20.0 | 50.0 |
| 28 | 4-t-$C_4H_9$ | 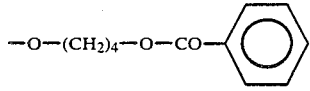 $-O-(CH_2)_4-O-CO-$ (phenyl) | 50 | 2.0 | 5.0 |
| Control | | | | | |
| 1 | Chlorphenesin | $-O-CH_2.CHOH.CH_2OH$ | 100 | 1.0 | 2.5 |
| 2 | Chromolyn sodium | | 250 | 0.4 | 1.0 | phenesin, Control 1, are inactive. This demonstrates that the $R_1$ substituent must be in the 4- or p- position, and that the COOH group imparts inactivity.

Of the thirteen 4-alkyl compounds tested, Example 7, the compound carrying the 4-tertiary-butyl group, was by far the most active. This shows that the alkyl group should be highly branched, and preferably tertiary, there being no difference between the 4-isopropyl and 4-n-propyl compounds (Examples 4 and 5). Surprisingly, the 4-isobutyl compound (Example 6) is inactive, under these test conditions.

The indane compound (Example 10) shows that the $R_1$ group can be condensed with the phenyl ring in an alkylene structure, since the indane compound is as effective as the three to five carbon atom alkyl compounds of Examples 5, 6, 8 and 9, having the same alkanol side chain.

The significance of the $R_3$ hydroxyl group is evident from Example 13, the 4-n-propyl compound in which the alkanol chain hydroxyl group is replaced by hydrogen. The activity is reduced by half at a doubled concentration, although the compound is still twice as effective as chlorphenesin.

EXAMPLES 15 to 28

Since the above results demonstrate the greatest effectiveness for the p-tertiary-butyl substituent, a second series of thirteen compounds were prepared, all p-tertiary-butyl phenoxy ethers having various alkanol or alkanol ester ($R_3$) substituents, as noted in Table II.

It is interesting to note from Examples 19 to 21 that activity is increased when the alkanol carbon chain is a straight chain having from six to eight carbon atoms. After eight carbon atoms, however, the activity diminishes markedly, and at eleven carbon atoms the compound is less effective than chlorphenesin.

Example 22 shows that branching in the alkanol chain reduces activity, although the activity is still four times greater than that of chlorphenesin.

Examples 26 and 27 show a most remarkable enhancing effect on activity upon esterification of the terminal hydroxyl group on the alkanol chain by nicotinic acid. Comparison of Examples 17 and 27 shows that the addition of the nicotinic acid group doubles the activity. This suggests that a compound in which the alkanol chain is from six to eight carbon atoms (as in Examples 19 and 20), if esterified with nicotinic acid would show an activity of forty times that of chlorphenesin. Similarly enhanced activities can be postulated by correlating the more active compounds in Table II with those combining substituents shown in the Table to give an enhanced activity.

The p-alkyl or cycloalkyl phenoxy alkanol ester can be administered to the animal by any available route, including oral and parenteral (intravenous, intraperitoneal, subcutaneous, and intramuscular) administration or by inhalation. The amount administered is sufficient to inhibit abnormal tissue reactivity due to specific allergic hypersensitivity or due to specific irritants by inhibiting the release of chemical mediators responsible for the symptoms of allergic diseases, irritation and inflammation produced by irritants and inflammation-causing substances. This amount will depend upon the species of animal, and the weight of the animal. For example, in human administration, a dosage of the alkanol or ester compound within the range from about 2 mg/kg to about 100 mg/kg per day should be sufficient. In the treatment of lower test animals, a similar dosage range is therapeutic. The upper limit of dosage is that imposed by toxic side effects, and can be determined by trial and error for the animal to be treated, including humans.

To facilitate administration, the p-alkyl or cycloalkyl phenoxy alkanol or ester compound can be provided in composition form, and preferably in dosage unit form. While the compound can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and nontoxic.

The carrier or diluent can be solid, semisolid, or liquid, and can serve as a vehicle, excipient, or medium for the p-alkyl or cycloalkyl phenoxy alkanol or ester compound. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl- and propyl-hydroxybenzoate, talc or magnesium stearate. Other agents that can be used for solubilizing or dispersing of compounds of this invention are dimethyl sulfoxide (DMSO), N,N-dimethyl acetamide (DMAC), propylene glycol and the polyoxyethylene ethers of hexitol fatty acid esters, such as sorbitol and mannitol esterified with lauric, stearic, palmitic or oleic acids, condensed with from ten to thirty moles of ethylene oxide. A commercially available material is Tween 80, a polyoxyethylene sorbitol oleate, the oleic acid ester of sorbitol condensed with twenty moles ethylene oxide per mole of sorbitol.

For convenience in handling, the p-alkyl or cycloalkyl phenoxy alkanol or ester compound and carrier or diluent can be enclosed or encapsulated in a capsule, sachet, cachet, gelatin, paper or other container, especially when intended for use in dosage units. The dosage units can for example take the form of tablets, capsules, suppositories or cachets.

The following Examples illustrate various forms of dosage units in which the p-alkyl or cycloalkyl phenoxy alkanol or ester compound can be prepared:

EXAMPLE A

| Tablet formulation | Mg/tablet |
| --- | --- |
| p-Alkyl or cycloalkyl phenoxy alkanol or ester compound | 15 |
| Lactose | 86 |
| Corn starch (dried) | 45.5 |
| Gelatin | 2.5 |
| Magnesium stearate | 1.0 |

The p-alkyl or cycloalkyl phenoxy alkanol or ester compound is powdered and passed through a mesh sieve and well mixed with the lactose and 30 mg of the corn starch, both passed through a sieve.

The mixed powders are massed with a warm gelatin solution prepared by stirring the gelatin in water and heating to form a 10% w/w solution. The mass is granulated by passing through a sieve, and the moist granules dried at 40° C.

The dried granules are regranulated by passing through a sieve and the balance of the starch and the magnesium stearate is added and thoroughly mixed.

The granules are compressed to produce tablets each weighing 150 mg.

EXAMPLE B

| Tablet formulation | Mg/tablet |
| --- | --- |
| p-Alkyl or cycloalkyl phenoxy alkanol or ester compound | 100 |
| Lactose | 39 |
| Corn starch (dried) | 80 |
| Gelatin | 4.0 |
| Magnesium stearate | 2.0 |

The method of preparation is identical with that of Example A except that 60 mg of starch is used in the granulation process and 20 mg during tabletting.

EXAMPLE C

| Capsule formulation | Mg/capsule |
| --- | --- |
| p-Alkyl or cycloalkyl phenoxy alkanol or ester compound | 250 |
| Lactose | 150 |

The p-alkyl or cycloalkyl phenoxy alkanol or ester compound and lactose are passed through a sieve and the powders well mixed together before filling into hard gelatin capsules of suitable size, so that each capsule contains 400 mg of mixed powders.

EXAMPLE D

| Suppositories | Mg/suppositories |
| --- | --- |
| p-Alkyl or cycloalkyl phenoxy alkanol or ester compound | 50 |
| Oil of Theobroma | 950 |

The p-alkyl or cycloalkyl phenoxy alkanol or ester compound is powdered and passed through a sieve and triturated with molten oil of theobroma at 45° C. to form a smooth suspension.

The mixture is well stirred and poured into molds, each of nominal 1 g capacity, to produce suppositories.

EXAMPLE E

| Cachets | Mg/cachet |
| --- | --- |
| p-Alkyl or cycloalkyl phenoxy alkanol or ester compound | 100 |
| Lactose | 400 |

The p-alkyl or cycloalkyl phenoxy alkanol or ester compound is passed through a mesh sieve, mixed with lactose previously sieved and fitted into cachets of suitable size so that each contains 500 mg.

EXAMPLE F

| Intramuscular injection (sterile suspension in aqueous vehicle) | Mg |
|---|---|
| p-Alkyl or cycloalkyl phenoxy alkanol or ester compound | 10 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

EXAMPLE G

| Intraperitoneal intraveneous or subcutaneous injection (sterile solution in aqueous carrier system) | Mg |
|---|---|
| p-Alkyl or cycloalkyl phenoxy alkanol or ester compound | 15 |
| Sodium citrate | 5.7 |
| Sodium carboxymethylcellulose (low viscosity grade) | 2.0 |
| Methyl para-hydroxybenzoate | 1.5 |
| Propyl para-hydroxybenzoate | 0.2 |
| Water for injection to 1.0 ml | |

Having regard to the foregoing disclosure, the following is claimed as patentable and inventive embodiments thereof:

1. A process for treating animals in need of antihistaminic treatment which comprises administering to the animal an amount therapeutically effective as an antihistamine of a p-alkyl or cycloalkyl phenoxy alkanol carbamic acid ester having the formula:

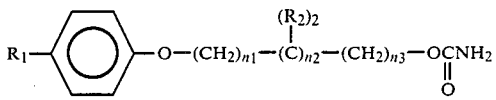

in which:

$R_1$ is an alkyl group having from one to six carbon atoms, or a bivalent cycloalkylene group having from five to seven ring carbon atoms and condensed with the phenyl group at adjacent ring carbons thereof that the cycloalkylene and phenyl rings share in common;

$R_2$ is lower alkyl having from one to three carbon atoms or hydrogen;

$n_1$, $n_2$ and $n_3$ represent the number of $CH_2$, $C(R_2)_2$ and $CH_2$ groups, respectively, and are numbers within the range from 0 to 10; and at least one of $n_1$, $n_2$ and $n_3$ is other than zero.

2. A process according to claim 1 in which the administration is orally.

3. A process according to claim 2 which comprises administering in dosage unit form.

4. A process according to claim 1 in which $R_1$ is tertiary alkyl, $n_2$ and $n_3$ are zero, and $n_1$ is from 2 to 8.

5. A process according to claim 1 in which $R_1$ is tert-butyl.

6. A process according to claim 1 in which $R_2$ is H.

7. A process according to claim 1 in which $R_1$ is tert-butyl and $R_2$ is H.

* * * * *